United States Patent [19]

Uno et al.

[11] Patent Number: 4,889,858
[45] Date of Patent: Dec. 26, 1989

[54] DIBENZ[B,E]OXEPIN DERIVATIVES AND PHARMACEUTICAL COMPOSITION CONTAINING THE SAME

[75] Inventors: Hitoshi Uno, Takatsuki; Mikio Kurokawa; Fuminori Sato, both of Kobe; Shunsuke Naruto, Ikoma; Yoshinobu Masuda, Katano, all of Japan

[73] Assignee: Dainippon Pharmaceutical Co., Ltd., Osaka, Japan

[21] Appl. No.: 180,104

[22] PCT Filed: Jun. 17, 1987

[86] PCT No.: PCT/JP87/00392

§ 371 Date: Feb. 17, 1988

§ 102(e) Date: Feb. 17, 1988

[87] PCT Pub. No.: WO87/07894

PCT Pub. Date: Dec. 30, 1987

[30] Foreign Application Priority Data

Jun. 17, 1986 [JP] Japan ............................ 61-142269

[51] Int. Cl.⁴ .................. A61K 31/495; C07D 405/04
[52] U.S. Cl. ..................................... 514/254; 544/364; 544/375; 549/354
[58] Field of Search ................. 544/364, 375; 514/254

[56] References Cited

U.S. PATENT DOCUMENTS 3,371,091 2/1968 Boissier et al. ........................ 544/374
3,929,791 12/1975 Gerecke et al. ...................... 544/375
3,985,750 10/1976 Protina et al. ....................... 544/375
4,082,850 4/1978 Lassman et al. ...................... 549/354
4,144,337 3/1979 Bastian ................................. 544/375
4,645,758 2/1987 Willman et al. ...................... 544/375

FOREIGN PATENT DOCUMENTS 853053 8/1985 South Africa .

OTHER PUBLICATIONS

Newman, M. S., and Wiseman, E. H., "Synthesis of 8-Fluoro-10-methyl-1,2-benzanthracene," *J. Org. Chem.* 26: 3208–3211, 1961.
Stach, K. and Spingler, H., "Development of Psychotropic Substances: New Ring Systems," *Monatsh. Chem.*, 93: 889–895, 1962.
Rajsner, M. and Provita, M., "Synthesis of 3,8-Difluoro-11-(3-dimethylamino propylidene)-6,11-dihydrodibenz[b,e]thiopins," *Coll. Czech. Commun.* 32: 2021–2024, 1967.
Swinyard, E. A., "Assay of Antiepileptic Drug Activity in Experimental Animals: Standard Tests," Anticonvulsant Drugs, Mercier, J., Ed., pp. 47–65, Pargamon Press, New York, 1973.
Linee et al., "Cerebral Metabolic, Hemodynamic and Antihypoxic Properties of 1-Eburnamonine," *Eur. Neurol. Supple* 1 17: 113–120, 1978.
Kubo et al., "Radical Scavenging Action of Flunarizine in Rat Brain in vitro," *Arch. Int. Pharmacodyn* 272: 283–295, 1984.
Wauquier, et al., "'Calcium Entry Blockers' as Cerebral Protecting Agents: Comparative Activity in Tests of Hypoxia and Hyperexcitability," *Japan J. Pharmacol.* 38: 1–7, 1985.

*Primary Examiner*—Glennon H. Hollrah
*Assistant Examiner*—James H. Turnipseed
*Attorney, Agent, or Firm*—Scully, Scott, Murphy & Presser

[57] ABSTRACT

The present invention relates to compounds represented by the general formula (I):

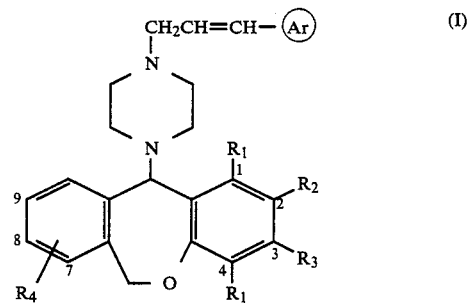

wherein $R_1$ is H or methoxy, $R_2$ is H, methoxy, OH or F, $R_3$ is H or F, $R_4$ is H or F at 7-, 8- or 9-position, and Ar is a benzene, thiophene or pyridine ring, provided that (i) at least two of $R_1$, $R_2$, $R_3$ and $R_4$ are H, (ii) $R_2$ or $R_3$ is F when $R_4$ is F, (iii) $R_1$, $R_3$ and $R_4$ are H when $R_2$ is methoxy or OH, (iv) $R_2$ and $R_3$ are not simultaneously F, and (v) $R_2$ and $R_3$ are H or F, and both $R_1$ and $R_4$ are H when Ar is a thiophene or pyridine ring, or a physiologically acceptable acid addition salt thereof. The compounds of the present invention have an excellent protective effect against cerebral anoxia and some of them have also an inhibitory effect on lipid peroxidation of mitochondrial membrane of brain and an anti-convulsant activity and are useful as an agent for prevention or treatment of cerebral diseases caused by hypoxia in mammals including human.

11 Claims, No Drawings

DIBENZ[B,E]OXEPIN DERIVATIVES AND PHARMACEUTICAL COMPOSITION CONTAINING THE SAME

FEATURES OF THE INVENTION

The present invention relates to novel dibenz[b,e]oxepin derivatives useful for prevention and treatment of cerebral diseases caused by hypoxia.

TECHNICAL BACKGROUND

The brain, different from other organs, exists under particular environment such that it is dipped in cerebrospinal fluid within rigid bodies such as the skull and pachymenix and is one of such organs as showing most active energy metabolism. The oxygen consumption rate of the brain is the highest among all of the organs. Most of energy required for cranial nerves cells are supplied with oxygen and glucose. Since these energy sources are scarcely stored in the brain, they are always supplied from blood. Therefore, mechanism for controlling cerebral blood flow in the cerebral blood vessel itself is well developed in order to stably supply energy source for the brain tissue and to keep the outer environment constant in the cranial nerves cells.

However, when the homeostatic mechanism is damaged in the brain by physical oppression such as cerebrovascular disorders, cerebral tumor or cerebral injury, the cranial nerves cells are exposed to hypoxic condition (cerebral anoxia/cerebral hypoxia) and cannot fulfill the normal function. Such condition of cerebral anoxia increases the production of various toxic active oxygen species. These activated oxygen species peroxidize membrane lipid of the cerebral mitochondria and it results in functional disturbance of the cranial nerves cells and finally a breakdown of the brain cells themselves. This gives such a vicious circle that the functional disturbance of the cranial nerves cells and the breakdown of the brain cells in turn induce severe cerebral anoxia This is the reason why the cerebral anoxia is called a common denominator of most disorders based on cerebral circulatory disturbances [Eur. Neurol., 17 (Supple. 1), 113 (1978)].

Under such circumstances, the present inventors have continuously studied to find compounds having an excellent protective effect against cerebral anoxia and preferably with an inhibitory effect on lipid peroxidation of brain mitochondria. The present inventors have finally succeeded in selection of novel dibenz[b,e]oxepin derivatives of the present invention and completed the present invention.

Prior arts relevant to the present invention include U.S Pat. No 4,144,337 and South African Pat. No. 85/3053.

In the above U.S. Pat. No. 4,144,337, the compounds having the following general formula (A) are disclosed.

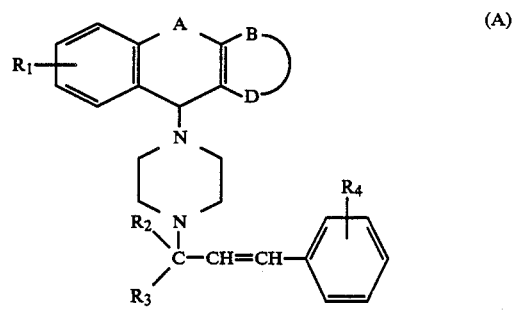
(A)

wherein each of $R_1$ and $R_4$, which may be the same or different, is hydrogen, halogen of atomic number from 9 to 35, alkyl of 1 to 4 carbon atoms or alkoxy of 1 to 4 carbon atoms, either each of $R_2$ and $R_3$ is hydrogen or $R_2$ and $R_3$ together are oxygen, either B and D together with the carbon atoms to which they are bound form a benzene ring, or B is sulphur and B and D together with the carbon atoms to which they are bound form a thiophene ring which may be substituted in the position α to the sulphur atom with halogen of atomic number from 9 to 35 or alkoxy of 1 to 4 carbon atoms, and when B and D together with the carbon atoms to which they are bound form a benzene ring, A is oxygen, sulphur, —CH₂—O— or —CH₂—S— in either orientation, or a group of formula

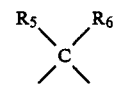

wherein each of $R_5$ and $R_6$, which may be the same or different, is alkyl of 1 to 4 carbon atoms, or when B is sulphur and B and D together with the carbon atoms to which they are bound form a substituted or unsubstituted thiophene ring, A is a group of formula

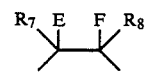

wherein each of $R_7$ and $R_8$, which may be the same or different, is hydrogen or alkyl of 1 to 4 carbon atoms and either each of E and F is hydrogen or E and F together form a bond.

Bearing in mind the structure of the compounds of the present invention, which will be fully explained hereinafter, detailed investigation of the very complicated substituents of the general formula (A) indicates that the general formula (A) covers an extremely small part of the compounds of the present invention. However, this U.S. patent does not disclose any example of the dibenz[b,e]oxepin derivatives. Further, although it is disclosed in this U.S. patent that the compounds specifically disclosed therein have psychostimulants and vigilance-increasing effect, these activities are completely different from those of the compounds of the present invention.

The above South African Pat. No. 85/3053 discloses the compounds represented by the following general formula (B).

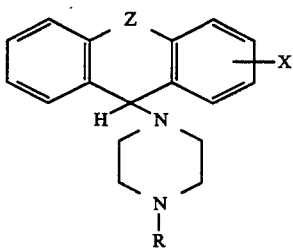

(B)

wherein X is hydrogen, halogen, lower alkoxy, lower alkylthio, lower alkylsulfonyl or trifluoromethyl, R is hydrogen, lower alkyl, cinnamyl, lower alkoxycinnamyl, cinnamoyl, lower alkoxycinnamoyl, lower hydroxyalkyl or carbalkoxy, Z is a saturated or unsaturated 2–3 atom chain in which no more than one atom of the chain is other than carbon and which optionally may be substituted with 1 to 2 halogen atoms.

The above general formula (B) contains a part of the compounds of the present invention. However, the South African Patent disclosing the above general formula (B) does not specifically disclose the compounds of the present invention. This South African Patent also discloses that a compound effective as inhibitors of calcium induced-contraction of vascular smooth muscle is useful for treatment of cardiovascular disorders as calcium entry blockers. However, the effect and the use disclosed in this literature are entirely different from those of the present invention.

DISCLOSURE OF THE INVENTION

The compounds of the present invention are the compounds represented by the following general formula (I) or a physiologically acceptable acid addition salt thereof:

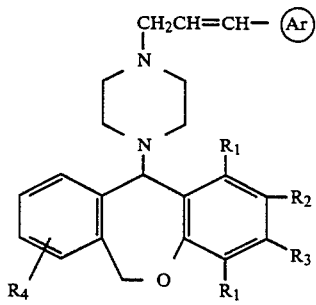

(I)

wherein $R_1$ is hydrogen atom or methoxy group, $R_2$ is hydrogen atom, methoxy group, hydroxy group or fluorine atom, $R_3$ is hydrogen atom or fluorine atom, $R_4$ is hydrogen atom or fluorine atom at 7-, 8- or 9-position, and (Ar) is a benzene ring, a thiophene ring or a pyridine ring, provided that (i) at least two of $R_1$, $R_2$, $R_3$ and $R_4$ are hydrogen atoms, (ii) $R_2$ or $R_3$ is fluorine atom when $R_4$ is fluorine atom, (iii) $R_1$, $R_3$ and $R_4$ are hydrogen atoms when $R_2$ is methoxy group or hydroxy group, (iv) $R_2$ and $R_3$ are not simultaneously fluorine atoms, and (v) $R_2$ is hydrogen atom or fluorine atom, $R_3$ is hydrogen atom or fluorine atom, and both $R_1$ and $R_4$ are hydrogen atoms when (Ar) is a thiophene ring or a pyridine ring.

The physiologically acceptable acid addition salts of the compounds of the present invention include, for example, inorganic acid salts such as hydrochloride, hydrobromide, hydroiodide, sulfate and phosphate, and organic acid salts such as oxalate, maleate, fumarate, lactate, malate, citrate, tartrate, benzoate and methanesulfonate. The compounds of the general formula (I) and the acid addition salts thereof may exist in the form of hydrate or solvate and these hydrate and solvate are also included in the compounds of the present invention.

Since the compounds of the general formula (I) have one asymmetric carbon atom and the substituent at 4-position of piperazine has one double bond, the compounds of the present invention can exist in the form of an optical isomer or a stereoisomer. These isomers and a mixture thereof are also included in the compounds of the present invention.

In viewpoint of the prior art, the compounds (I) of the present invention are divided into two groups. One of the groups is represented by the following general formula (I-a):

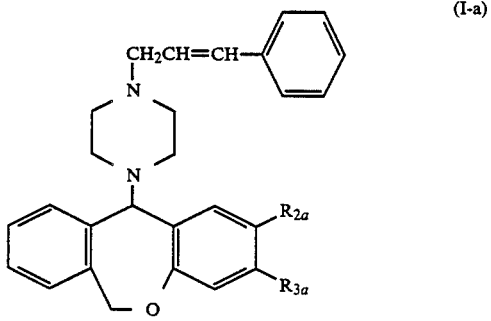

(I-a)

wherein $R_{2a}$ is hydrogen atom or methoxy group, and $R_{3a}$ is hydrogen atom or fluorine atom, provided that at least one of $R_{2a}$ and $R_{3a}$ is always hydrogen atom.

The compound of the present invention having the above general formula (I-a) is conceptually included in the compounds of the general formulas (A) and (B) disclosed in the above U.S. patent and the South African Patent. However, as is already mentioned, the compound (I-a) is not specifically disclosed in these two patents and the action specifically disclosed in these two patents and that of the compounds of the present invention are entirely different from each other.

The other group of the compounds of the present invention is represented by the following general formula (I-b):

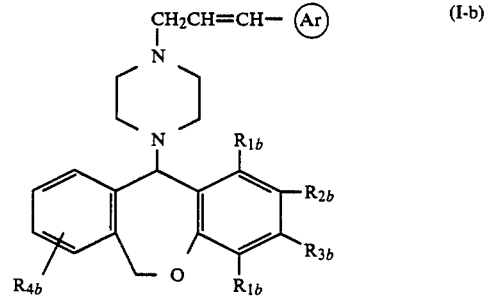

(I-b)

wherein $R_{1b}$ is hydrogen atom or methoxy group, $R_{2b}$ is hydrogen atom, hydroxy group or fluorine atom, $R_{3b}$ is hydrogen atom or fluorine atom, $R_{4b}$ is hydrogen atom or fluorine atom at 7-, 8- or 9-position, and (Ar) is a benzene ring, a thiophene ring or a pyridine ring, provided that (i) at least two of $R_1b$, $R_2b$, $R_3b$ and $R_4b$ are hydrogen atoms, (ii) $R_2b$ or $R_3b$ is fluorine atom when $R_4b$ is fluorine atom, (iii) $R_1b$, $R_3b$ and $R_4b$ are hydrogen atoms when $R_2b$ is hydroxy group, (iv) $R_2b$ and $R_3b$ are not simultaneously fluorine atoms, (v) $R_2b$ is hydrogen atom or fluorine atom, $R_3b$ is hydrogen atom or fluorine atom, and $R_1b$ and $R_4b$ are both hydrogen atoms when (Ar) is a thiophene ring or a pyridine ring, and further excluding the compound in which (Ar) is a benzene ring, $R_3b$ is fluorine atom, and $R_1b$, $R_2b$ and $R_4b$ are hydrogen atoms.

The compounds of the present invention represented by the general formula (I-b) are novel compounds which are never disclosed conceptually or specifically in the above U.S. patent and the South African Patent.

The compounds (I) of the present invention have an excellent protective effect against cerebral anoxia, and some of them have also an inhibitory effect on lipid peroxidation of brain mitochondria and an anti-convulsant activity. The compounds (I) of the present invention wherein $R_2$ is methoxy group can be converted into the compounds wherein $R_2$ is hydroxy group, which have a more strong inhibitory effect on lipid peroxidation of brain mitochondria, through metabolism in the living body. In the compounds (I) of the present invention, a conformation with respect to the double bond is preferably a trans form, that is E form. Among the compounds of the present invention, the following compounds and physiologically acceptable salts thereof are especially preferable:

11-(4-Cinnamyl-1-piperazinyl)-3-fluoro-6,11-dihydrodibenz[b,e]oxepin
11-(4-Cinnamyl-1-piperazinyl)-2-methoxy-6,11-dihydrodibenz[b,e]oxepin
11-(4-Cinnamyl-1-piperazinyl)-2-hydroxy-6,11-dihydrodibenz[b,e]oxepin The pharmacological activities of the compounds of the present invention are illustrated by the following pharmacological tests on the compounds of the present invention (Nos. 1–9), the compounds A and B which are not included in the present invention (see Reference Examples 9 and 10 described hereinafter), and flunarizine hydrochloride which is a commercially available drug useful for the treatment of cerebrovascular disorders.

EXPERIMENT 1

Protective Effect Against Cerebral Anoxia (1) Prolonging effect of the persistent time of gasping movements in complete ischemia Test was conducted in accordance with the procedure by Wauquier et al. [Japan J. Pharmacol., 38, 1 (1985)], employing five ddY male mice weighing 20–24 g in each group. Test compounds were suspended in 0.5% tragacanth solution and then a fixed amount of the suspension was orally administered to mice in an amount of 0.1 ml/10 g body weight, while the same amount of 0.5% tragacanth solution was orally administered to control group. Two hours after the administration of the test compounds, the necks of mice were cut with scissors for decapitation. The persistent of gasping movements of isolated heads was measured and minimal effective dose was determined by statistically comparing with the data in control group. The results are shown in Table 1.

As shown in Table 1, the activities of the compounds of the present invention (No.1–9) are equipotent to or much more excellent than flunarizine hydrochloride. In contrast, the compounds A and B not included in the present invention have lower activities.

TABLE 1

Prolonging Effect of the Persistent of Gasping Movements in Complete Ischemia

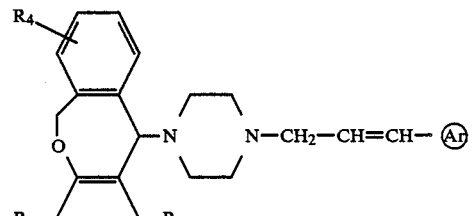

| No. | $R_1$ | $R_2$ | $R_3$ | $R_4$ | (Ar) | n | Q | Minimal Effective Dose |
|---|---|---|---|---|---|---|---|---|
| 1 | H | H | F | H | ph | 1 | 3/2 maleate | 10 |
| 2 | H | MeO | H | H | ph | 0 | 2 fumarate | 3 |
| 3 | H | OH | H | H | ph | 0 | fumarate | 30 |
| 4 | H | F | H | F (8-pos.) | ph | 0 | 2 maleate | 30 |
| 5 | H | H | F | F (7-pos.) | ph | ½ | 2 oxalate | 3 |
| 6 | H | H | F | F (9-pos.) | ph | 0 | 2 maleate | 10 |
| 7 | MeO | H | H | H | ph | ½ | 3 maleate | 30 |
| 8 | H | F | H | H | 2-T | ½ | 2 oxalate | 30 |
| 9 | H | F | H | H | 3-P | ½ | 2 oxalate | 30 |

TABLE 1-continued

Prolonging Effect of the Persistent of Gasping Movements in Complete Ischemia

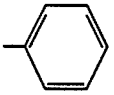

| No. | R₁ | R₂ | R₃ | R₄ | (Ar) | n | Q | Minimal Effective Dose (mg/kg) |
|---|---|---|---|---|---|---|---|---|
| A | H | H | F | H | ![OMe-phenyl] | 0 | 2 maleate | >100 |
| B | H | H | Me | H | ph | ½ | 2 oxalate | >100 |
| Flunarizine hydrochloride | | | | | | | | 30 | ph: phenyl, 2-T: 2-thienyl, 3-P: 3-pyridyl, MeO: methoxy, Me: methyl (2) Prolonging effect on the time to death by hypoxia in mice Five STD-ddY male mice (weighing 20-24 g) were employed in each group. A fixed amount of test compounds was suspended in 0.5% tragacanth solution and the suspension was orally administered to mice in an amount of 0.1 ml/10 g body weight. Two hours after the administration, each mouse was taken in a 2.5 liter plastic chamber and a mixed gas comprising 4% oxygen and 96% nitrogen was passed through the chamber at a rate of 4 liter/min. There was measured the time till the death (respiratory cessation) of mice. To control group, a 0.5% tragacanth solution without test compound was orally administered. The results are shown in Table 2.

TABLE 2

Prolonging Effect on the Time to Death by Anoxia in Mice

| No. | R₁ | R₂ | R₃ | R₄ | (Ar) | n | Q | Score* |
|---|---|---|---|---|---|---|---|---|
| 1 | H | H | F | H | ph | 1 | 3/2 maleate | ++(100) |
| 2 | H | MeO | H | H | ph | 0 | 2 fumarate | ++(30) |
| A | H | H | F | H | ![OMe-phenyl] | 0 | 2 maleate | −(100) |
| B | H | H | Me | H | ph | ½ | 2 oxalate | 0(100) |
| Flunarizine hydrochloride | | | | | | | | 0(100) | ph: phenyl, MeO: methoxy, Me: methyl
*Score
++(100): showing a prolonging effect at a dose of 100 mg/kg
++(30): showing a prolonging effect at a dose of 30 mg/kg
−(100): showing shorter survival time compared with control group at a dose of 100 mg/kg
0(100): showing no prolonging effect at a dose of 100 mg/kg As shown in Table 2, the prolonging effect under hypoxic condition of the compounds 1 and 2 of the present invention is clearly more excellent than that o flunarizine hydrochloride.

EXPERIMENT 2

Inhibitory Effect on Lipid Perioxidation of Brain Mitochondria

This test was conducted in accordance with the procedures by Kubo et al. [Arch. int. Pharmacodyn., 272, 283 (1984)]. Brain mitochondria of rat were incubated in 25 mM Tris-HCl buffer solution at 37° C. for 30 minutes in the presence of $Fe^{++}$ ion (25 μM) and ascorbic acid (50 μM), and the produced peroxidized lipid was measured by the thiobarbituric acid method. A concentration of the test compounds to inhibit the production of peroxidized lipid by 50% (IC$_{50}$) was calculated. The results are shown in Table 3.

TABLE 3

Inhibitory Effect on Lipid Peroxidation of Brain Mitochondria

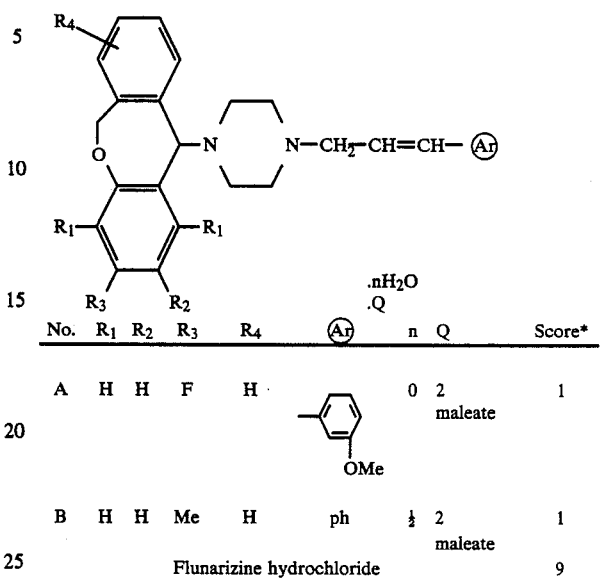

| No. | $R_1$ | $R_2$ | $R_3$ | $R_4$ | (Ar) | n | .nH$_2$O .Q | IC$_{50}$ (μM) |
|---|---|---|---|---|---|---|---|---|
| 1 | H | H | F | H | ph | 1 | 3/2 maleate | 7.8 |
| 3 | H | HO | H | H | ph | 0 | fumarate | 12.3 |
| A | H | H | F | H | ◯-OMe | 0 | 2 maleate | >150 |
| B | H | H | Me | H | ph | ½ | 2 oxalate | >150 |
| Flunarizine hydrochloride | | | | | | | | 3.3 | ph: phenyl, MeO: methoxy, Me: methyl

EXPERIMENT 3

Anti-convulsant Activity

Three ddY male mice weighing 20-24 g were employed in each group. Test compounds suspended in a 0.5% tragacanth solution were orally administered to mice at a dose of 100mg/kg in an amount of 0.1 ml/10 g body weight. The same amount of 0.5% tragacanth solution was orally administered to control group. Two hours after the administration of the test compounds, the anti-convulsant activity was measured in accordance with the procedure by Swinyard (Mercier, J., Ed., "Anticonvulsant Drugs", P. 47–65, Pargamon Press, New York, 1973). The results are shown in Table 4.

TABLE 4

Anti-convulsant Activity

| No. | $R_1$ | $R_2$ | $R_3$ | $R_4$ | (Ar) | n | .nH$_2$O .Q | Score* |
|---|---|---|---|---|---|---|---|---|
| 1 | H | H | F | H | ph | 1 | 3/2 maleate | 9 |
| 4 | H | F | H | F (8-pos.) | ph | 0 | 2 fumarate | 9 |

TABLE 4-continued

Anti-convulsant Activity

| No. | $R_1$ | $R_2$ | $R_3$ | $R_4$ | (Ar) | n | .nH$_2$O .Q | Score* |
|---|---|---|---|---|---|---|---|---|
| A | H | H | F | H | ◯-OMe | 0 | 2 maleate | 1 |
| B | H | H | Me | H | ph | ½ | 2 maleate | 1 |
| Flunarizine hydrochloride | | | | | | | | 9 | ph: phenyl, MeO: methoxy, Me: methyl
*Score
9: Anti-convulsant activity was observed in all three mice.
1: No anti-convulsant activity was observed in all three mice.

EXPERIMENT 4

Acute Toxicity

Five ddY male mice weighing 20-24 g were employed in each group. The compound 1 of the present invention suspended in a 0.5% tragacanth solution was orally administered to mice at a dose of 500 mg/kg in an amount of 0.1 ml/10 g body weight. After the administration, the occurrence of death has been observed for seven days. The result showed no death of the animal.

The process for preparing the compounds of the present invention is illustrated.

The compounds (I) of the present invention or the physiologically acceptable acid addition salts thereof can be prepared by either the following process (a) or (b).

Process (a)

The compounds (I) of the present invention can easily be prepared by reacting a compound having the general formula (II):

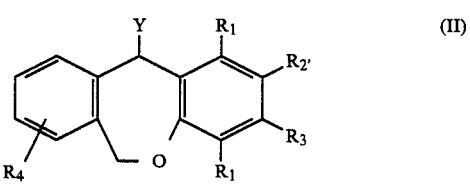

wherein Y is a reactive ester residue of an alcohol, $R_2'$ is hydrogen atom, methoxy group, or hydroxy group which may be protected or fluorine atom, and $R_1$, $R_3$ and $R_4$ are the same as defined in the general formula (I), with a compound having the general formula (III)

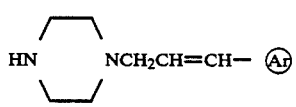 (III)

wherein Ar is the same as defined in the general formula (I), and removing the protecting group if present in the product.

The protecting group for hydroxy group in $R_2'$ of the general formula (II) may be any group if it can be removed without destroying the structure of the compounds of the present invention formed by the reaction. Such protecting group includes acyl groups such as acetyl or alkylsilyl groups such as trimethylsilyl or dimethyl-t-butylsilyl group. Among them, dimethyl-t-butylsilyl group is preferable since it can be removed in the presence of fluoride ion under a neutral condition. The reactive ester residue of an alcohol represented by Y in the general formula (II) includes halogen atoms such as chlorine or bromine, lower alkylsulfonyloxy groups such as methanesulfonyloxy or ethanesulfonyloxy, arylsulfonyloxy groups such as benzene sulfonyloxy, p-toluenesulfonyloxy or m-nitro benzene sulfonyloxy, and the like.

The reaction between the compound of the general formula (II) and the compound of the general formula (III) is carried out in the absence of a solvent or in the presence of a suitable solvent. Examples of the solvent are aromatic hydrocarbons such as benzene, toluene and xylene, halogenated hydrocarbons such as methylene chloride and chloroform, ketones such as methyl ethyl ketone, ethers such as tetrahydrofuran and dioxane, acetonitrile, dimethylformamide, and the like. These solvents may be employed alone or in a mixture of two or more thereof. The reaction is preferably carried out in the presence of a base. Examples of the base are organic bases such as triethylamine, tributylamine, diisopropylethylamine and N-methylmorpholine. An excess amount of the compound of the general formula (III) also acts as the base. The reaction temperature is usually from about 0° to about 80° C.

The removal of the protecting group for hydroxy group in $R_2'$ can be carried out by any suitable procedure depending on the properties of the protecting group. For example, the compound having dimethyl-t-butylsilyl group as the protecting group is dissolved in an organic solvent and thereto a substance having fluoride ion such as tetra-n-butyl ammonium fluoride is added and the mixture is stirred at room temperature, by which the protecting group can easily be removed.

Process (b)

The compounds (I) of the present invention can easily be prepared by reacting a compound represented by the following general formula (IV)

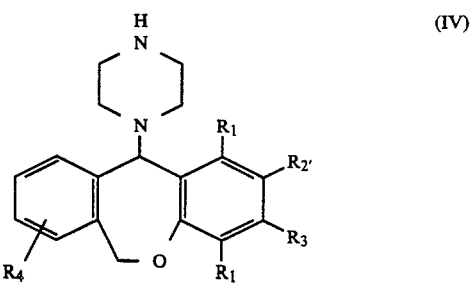 (IV)

wherein $R_2'$ is the same as defined in the general formula (II), $R_1$, $R_3$ and $R_4$ are the same as defined in the general formula (I), with a compound represented by the following general formula (V)

 (V)

$Z-CH_2CH=CH-$ Ar wherein Z is a reactive ester residue of an alcohol, and Ar is the same as defined in the general formula (I), and removing the protecting group if present in the product.

In the general formula (V), the reactive ester residue of an alcohol represented by Z includes the same groups or atoms as mentioned in the above process (a).

The reaction between the compound of the general formula (IV) and the compound of the general formula (V) is carried out in the absence of a solvent or in the presence of the same solvent as mentioned in the process (a) and preferably in the presence of a base. The base includes alkali hydrogen carbonates such as sodium hydrogen carbonate and potassium hydrogen carbonate, and alkali carbonates such as sodium carbonate and potassium carbonate in addition to the organic base mentioned in the process (a). The reaction temperature is usually from about 0° to about 160° C. When the compound wherein Z in the general formula (V) is chlorine or bromine is employed, the addition of alkali metal iodides such as sodium iodide and potassium iodide promotes the reaction more smoothly. The protecting group in $R_2'$ is the same as mentioned in the process (a) and can be removed in the same manner as mentioned in the process (a).

The compounds of the general formula (I) of the present invention formed by the above processes are isolated and purified by the conventional procedure such as chromatography, recrystallization or reprecipitation.

The compounds of the general formula (I) are obtained in the form of a free base or an acid addition salt, depending on the selection of the starting compound, the reaction condition or the treating condition. The acid addition salt can be converted into the free base by the conventional procedure, for example, by treating the salt with a base such as an alkali carbonate. On the other hand, the free base can be converted into the acid addition salt by treating the base with various acids in accordance with the conventional process.

The starting compounds (II) and (IV) can be prepared by the processes of the following Reference Examples or in a similar manner.

Since the thus obtained compounds (I) of the present invention or the physiologically acceptable acid addition salts thereof have an excellent protective effect against cerebral anoxia and some of them have also an inhibitory effect on lipid peroxidation of mitochondrial membrane of brain and an anti-convulsant activity, they are especially useful for the protection and/or the treatment of cerebral diseases caused by hypoxia, such as cerebrovascular disorders (e.g. cerebral infraction, cerebral hemorrhage and cerebral arteriosclerosis), cerebral tumor and cerebral injury.

The compounds of the general formula (I) and the physioligically acceptable acid addition salts thereof may be administered by means of any of oral, parenteral or intrarectal administration, preferably by oral administration. Although the dose is varied depending on the kinds of the compounds, the administration routes, the conditions and the age of the patients and the like, it is usually 0.005-20 mg/kg/day. The compounds of the general formula (I) or the acid addition salts thereof are usually administered in the form of pharmaceutical preparations prepared by mixing with a pharmaceutical carrier. The pharmaceutical carrier includes substances which are commonly used in the pharmaceutical field and do not react with the compounds of the general formula (I) or the acid addition salts thereof. Examples thereof are, lactose, glucose, mannitol, dextrin, cyclodextrin, starch, sucrose, magnesium metasilicate aluminate, synthetic aluminium silicate, crystalline cellulose, sodium carboxymethyl-cellulose, calcium carboxymethylcellulose, ion exchange resin, methylcellulose, gelatin, gum arabic, Pullulan, hydroxypropyl cellulose, low-substituted hydroxypropyl cellulose, hydroxypropyl methyl cellulose, polyvinylpyrrolidone, polyvinyl alcohol, light silicic anhydride, magnesium stearate, talc, tragacanth, bentonite, bee gum, carboxyvinyl polymer, titanium oxide, sorbitan fatty acid esters, sodium laurylsulfate, glycerin, glycerin fatty acid esters, purified lanolin, glycero-gelatin, polysorbate, macrogol, vegetable oil, wax, propylene glycol, water and the like. Dosage forms include tablets, capsules, granules, powders, syrups, suspensions, injections, suppositories and the like. These pharmaceutical preparations are prepared in accordance with the conventional procedures. Liquid preparations may be dissolved or suspended in water or other suitable mediums when used. Tablets and granules may be coated by the known method.

These pharmaceutical preparations can contain not less than 0.5%, preferably from 1-70% of the compound of the general formula (I) or the physiologically acceptable acid addition salt thereof. These pharmaceutical preparations may contain other components which are valuable in the treatment.

BEST MODE FOR WORKING OF THE INVENTION

The present invention is illustrated by the following Reference Examples and Examples. The identification of the compound was carried out by elementary analysis, mass spectrum, IR spectrum, NMR spectrum and the like.

The conformation concerning the double bond is an E form (trans form) unless specified otherwise.

REFERENCE EXAMPLE 1

Preparation of 11-chloro-3-fluoro-6,11-dihydrodibenz[b,e]oxepin:

To a solution of 5.2 g of sodium metal in 300 ml of ethanol is added 25 g of 3-fluorophenol. The solvent is distilled off under reduced pressure. To the residue is added 25 g of phthalide and the mixture is stirred at 200° C. for 1 hour with heating. After cooling to 100° C., 500 ml of water is added to dissolve and thereto 10% hydrochloric acid is added under ice cooling to make the solution acidic to precipitate a crystalline product, which is filtered, washed with water and dried to give 42 g of 2-[(3-fluorophenyloxy)methyl]benzoic acid. Mass spectrum m/z: 246(M+).

To 250 g of phosphorus pentoxide is slowly added 160 ml of ethanol at room temperature. The mixture is further stirred with heating at 100° C. for 1 hour. Thereto 42 g of 2-[(3-fluorophenyloxy)methyl]benzoic acid is added and the mixture is stirred with heating at 100° C. for 1 hour. After cooling to room temperature, 500 ml of water is added. After extraction with toluene, washing successively with saturated sodium hydrogen carbonate, water and a saturated saline solution and drying over magnesium sulfate, the solvent is distilled off under reduced pressure to give 31 g of 3-fluoro-6,11-dihydrodibenz[b,e]oxepin-11-one (oil). Mass spectrum m/z: 228(M+).

To a solution of 2.0 g of 3-fluoro-6,11-dihydrodibenz[b,e]oxepin-11-one in 20 ml of methanol is added 0.5 g of sodium borohydride with ice-cooling and then the mixture is stirred at the same temperature for 1 hour. The reaction mixture is poured into water and the resultant is extracted with toluene. The extract is washed with water and then dried over magnesium sulfate. Toluene is distilled off to give 1.9 g of 3-fluoro-6,11-dihydrodibenz[b,e]oxepin-11-ol (crystals). Mass spectrum m/z: 230(M+).

To a solution of 1.5 g of 3-fluoro-6,11-dihydrodibenz[b,e]oxepin-11-ol in 20 ml of methylene chloride is added dropwise a solution of 1.6 g of thionyl chloride in 10 ml of methylene chloride under ice cooling over 30 minutes and then the mixture is stirred at room temperature for 1 hour. The reaction mixture is concentrated at room temperature under reduced pressure to give 1.5 g of 11-chloro-3-fluoro-6,11-dihydrodibenz[b,e]oxepin (oil). Mass spectrum m/z: 248(M+)

REFERENCE EXAMPLE 2

Preparation of 2-methoxy-6,11-dihydrodibenz[b,e]oxepin-11-ol:

A solution of 10 g of 2-methoxy-6,11-dihydrodibenz[b,e]oxepin-11-one [Monatsh. Chem., 93, 889 (1962)] in 100 ml of methanol is cooled to 0° C. Thereto 3 g of sodium borohydride is added and the mixture is stirred for 1 hour. After completion of the reaction, chloroform is added and the mixture is washed with a saturated saline solution. After drying over magnesium sulfate and the solvent is distilled off under reduced pressure, the residue is subjected to a silica-gel chromatography and eluted with toluene to give 9 g of the objective compound as an oily product. Mass spectrum m/z: 242(M+).

REFERENCE EXAMPLE 3

Preparation of 2-(dimethyl-t-butylsilyloxy)-6,11-dihydrodibenz[b,e]oxepin-11-ol:

A mixture of 20 g of 2-methoxy-6,11-dihydrodibenz[b,e]oxepin-11-one and 150 g of pyridine hydrochloride is stirred with heating at 180° C for 2 hours. The solution is poured into 2 liter of water with stirring to give 15 g of 2-hydroxy-6,11-dihydrodibenz[b,e]oxepin- 11-one. Mass spectrum m/z: 226(M+), melting point: 165°–166° C. (recrystallized from ethanol).

To a solution of 10 g of 2-hydroxy-6,11-dihydrodibenz[b,e]oxepin-11-one in 50 ml of dimethylformamide are added 6.5 g of imidazole and 7 g of t-butyldimethylchlorosilane and the mixture is stirred for 1 hour. After adding 300 ml of toluene, successively washing with water and a saturated saline solution and drying over magnesium sulfate, the solvent is distilled off under reduced pressure to give 13 g of 2-(dimethyl-t-butylsilyloxy)-6,11-dihydrodibenz[b,e]oxepin-11-one (oil). Mass spectrum m/z: 340(M+).

A solution of 5 g of 2-(dimethyl-t-butylsilyloxy)-6,11-dihydrodibenz[b,e]oxepin-11-one in 50 ml of methanol is cooled to 0° C. After adding 2 g of sodium borohydride and the mixture is stirred for 1 hour, 300 ml of chloroform is added and the mixture is washed with water and a saturated saline solution, followed by drying over magnesium sulfate. The solvent is distilled off under reduced pressure and the residue is subjected to silica-gel chromatography and eluted with toluene to give 4.1 g of 2-(dimethyl-t-butylsilyloxy)-6,11-dihydrodibenz[b,e]oxepin-11-ol (oil). Mass spectrum m/z: 342(M+).

REFERENCE EXAMPLE 4

Preparation of 3,7-difluoro-6,11-dihydrodibenz[b,e]oxepin-11-one:

To a solution of 10 g of 3-fluoro-2-methylbenzoic acid [J. Org. Chem., 26, 3208 (1961)]in 300 ml of dimethylformamide are added 30 g of potassium carbonate and 30 g of ethyl iodide and the mixture is stirred at room temperature for 8 hours. After adding 500 ml of toluene, washing with water and a saturated saline solution and drying over magnesium sulfate, the solvent is distilled off under reduced pressure to give 11 g of ethyl 3-fluoro-2-methylbenzoate (oil). Mass spectrum m/z: 182(M+).

To a solution of 11 g of ethyl 3-fluoro-2-methylbenzoate in 300 ml of carbon tetrachloride is added 12 g of N-bromosuccinimide and the mixture is refluxed with heating for 12 hours. After cooling, the mixture is washed with water and a saturated saline solution and dried over magnesium sulfate and the solvent is distilled off under reduced pressure to give 13 g of ethyl 3-fluoro-2-bromomethylbenzoate. Mass spectrum m/z: 262, 260(M+).

To a solution of 1.3 g of sodium metal in 100 ml of ethanol are added 6.3 g of 3-fluorophenol and 13 g of ethyl 3-fluoro-2-bromomethylbenzoate and the mixture is refluxed with heating for 8 hours. After cooling, 300 ml of water is added and the mixture is extracted with toluene. After the extract is washed with water and a saturated saline solution and dried over magnesium sulfate, the solvent is distilled off under reduced pressure. The residue is subjected to silica-gel chromatography and eluted with toluene to give 13 g of ethyl 3-fluoro-2-[(3-fluorophenyl oxy)methyl]benzoate (oil). Mass spectrum m/z: 292(M+).

To a solution of 13 g of ethyl 3-fluoro-2-[(3-fluorophenyloxy)methyl]benzoate in 100 ml of ethanol is added 50 ml of 5% aqueous solution of sodium hydroxide and the mixture is refluxed with heating for 1 hour. After the solvent is distilled off under reduced pressure, 300 ml of water is added and then 10% hydrochloric acid is added to make the mixture acidic. The precipitated crystals are collected by filtration and dried to give 11 g of 3-fluoro-2-[3-fluorophenyloxy)methyl]benzoic acid. Mass spectrum m/z: 264(M+).

A mixture of 7 g of 3-fluoro-2-[(3-fluorophenyloxy)methyl]benzoic acid and 50 g of thionyl chloride is refluxed with heating for 1 hour. After cooling to room temperature, dry toluene is added and the solvent is distilled off under reduced pressure. The residue is added with dichloromethane and the mixture is cooled to 0° C. Thereto 6 g of powdery anhydrous aluminum chloride is added and the mixture is stirred for 15 minutes and then added with ice-water, followed by extraction with toluene. After drying the extract over magnesium sulfate, the solvent is distilled off under reduced pressure. The residue is subjected to silica-gel chromatography and eluted with toluene to give 4.0 g of 3,7-difluoro-6,11-dihydrodibenz[b,e]oxepin-11-one (oil). Mass spectrum m/z: 246(M+).

REFERENCE EXAMPLE 5

Preparation of 3,9-difluoro-6,11-dihydrodibenz[b,e]oxepin11-one:

To a solution of 1.5 g of sodium metal in 100 ml of ethanol are added 8 g of 3-fluorophenol and 17 g of ethyl 5-fluoro-2-bromomethylbenzoate [U.S. Pat. No. 4,082,850]and the mixture is refluxed with heating for 8 hours. After cooling, 300 ml of water is added and the mixture is extracted with toluene. The extract is washed with water and a saturated saline solution and dried over magnesium sulfate. The solvent is distilled off under reduced pressure to give 20 g of ethyl 5-fluoro-2-[(3-fluorophenyl oxy)methyl]benzoate (oil). Mass spectrum m/z: 292(M+).

To a solution of 15 g of ethyl 5-fluoro-2-[(3-fluorophenyloxy)methyl]benzoate in 200 ml of ethanol is added 100 ml of 5% aqueous sodium hydroxide and the mixture is refluxed with heating for 1 hour. After cooling, the solvent is distilled off under reduced pressure and the residue is added with 300 ml of water and then with 10% hydrochloric acid to make the mixture acidic. The precipitated crystals are collected by filtration and dried to give 12 g of 5-fluoro-[(3-fluorophenyloxy)methyl]benzoic acid. Mass spectrum m/z: 264(M+).

To 10 g of 5-fluoro-2-[(3-fluorophenyloxy)methyl]benzoic acid is added 50 g of thionyl chloride and the mixture is refluxed with heating for 1 hour. After cooling the reaction mixture to room temperature, dry toluene is added and the solvent is distilled off under reduced pressure. The residue is added with dichloromethane and cooled to 0° C. Thereto 10 g of powdery anhydrous aluminum chloride is added and the mixture is stirred for 15 minutes. The reaction mixture is added with ice-water and extracted with toluene. After the extract is dried over magnesium fulfate, the solvent is distilled off under reduced pressure and the residue is subjected to silica-gel chromatography, followed by elution with toluene to give 4.3 g of 3,9-difluoro-6,11-dihydrodibenz[b,e]oxepin-11-one (oil). Mass spectrum m/z: 246(M+).

REFERENCE EXAMPLE 6

Preparation of 2,8-difluoro-6,11-dihydrodibenz[b,e]oxepin-11-one:

To a solution of 2.0 g of sodium metal in 100 ml of ethanol is added 10.0 g of 4-fluorophenol and the solvent is distilled off under reduced pressure. To the residue is added 12 g of 5-fluorophthalide [Coll. Czech. Commun., 32, 2021 (1967)]and the mixture is stirred with heating at 200° C. for 1 hour. The mixture is cooled to 100° C. and dissolved in 300 ml of water. This solution is made acidic by adding 10% hydrochloric acid under ice cooling to precipitate crystals of the objective compound, which are collected by filtration, washed with water and dried to give 17 g of 4-fluoro-2-[(4-fluorophenyloxy)methyl]benzoic acid. Mass spectrum m/z: 264(M+).

To 15 g of 4-fluoro-2-[(4-fluorophenyoxy)methyl]-benzoic acid is added 60 g of thionyl chloride and the mixture is refluxed with heating for 1 hour. After cooling the reaction mixture to room temperature, dry toluene is added and the solvent is distilled off under reduced pressure. The residue is added with dichloromethane and the mixture is cooled to 0° C. and added with 15 g of powdery anhydrous aluminum chloride, which is stirred for 15 minutes. The reaction mixture is added with ice-water and extracted with toluene. After the extract is successively washed with water and a saturated saline solution and dried over magnesium sulfate, the solvent is distilled off under reduced pressure. The residue is subjected to silica-gel chromatography and eluted with toluene to give 9.1 g of 2,8-difluoro-6,11-dihydrodibenz[b,e]oxepin-11-one (oil). Mass spectrum m/z: 246(M+).

REFERENCE EXAMPLE 7

Preparation of 1,4-dimethoxy-6,11-dihydrodibenz[b,e]oxepin-11-one:

To a solution of 1.5 g of sodium metal in 100 ml of ethanol is added 10 g of 2,5-dimethoxyphenol and the solvent is distilled off under reduced pressure. The residue is added with 7.2 g of phthalide and the mixture is stirred with heating at 200° C. for 1 hour. The reaction mixture is cooled to 100° C. and dissolved in 300 ml of water. This solution is made acidic by adding 10% hydrochloric acid under ice cooling to precipitate crystals of the objective compound, which are collected by filtration, washed with water and dried to give 14 g of 2-[(2,5-dimethoxyphenyloxy)methyl]benzoic acid. Mass spectrum m/z: 288(M+).

To 50 g of phosphorus pentoxide is slowly added 30 ml of ethanol at room temperature and the mixture is further stirred with heating at 100° C. for 1 hour. Thereto 10 g of 2-[(2,5-dimethyoxyphenyloxy)methyl]benzoic acid is added and the mixture is stirred at 100° C. for 1 hour. After cooling to room temperature, the mixture is added with 300 ml of water and extracted with toluene. After the extract is successively washed with a saturated solution of sodium hydrogen carbonate, water and a saturated saline solution and dried over magnesium sulfate, the solvent is distilled off under reduced pressure to give 7 g of 1,4-dimethoxy-6,11-dihydrodibenz[b,e]oxepin-11-one (oil). Mass spectrum m/z: 270(M+).

REFERENCE EXAMPLE 8

Preparation of 2-fluoro-11-(1-piperazinyl)-6,11-dihydrodibenz[b,e]oxepin:

To a solution of 15 g of 11-chloro-2-fluoro-6,11-dihydrodibenz[b,e]oxepin, which is prepared according to the procedure of Reference Example 1, in 300 ml of chloroform is added a solution of 25 g of anhydrous piperazine in 50 ml of chloroform at 0° C. After the temperature of the reaction mixture is raised to room temperature over 2 hours, it is added with 10% aqueous sodium hydroxide and extracted with chloroform. After the extract is washed with a saturated saline solution and dried over anhydrous potassium carbonate, the solvent is distilled off under reduced pressure. After the residue is added with 500 ml of toluene, an excess amount of piperazine is distilled off under reduced pressure to give 12 g of the objective compound as an oil. Mass spectrum m/z:298(M+).

EXAMPLE 1

Preparation of 11-(4-cinnamyl-1-piperazinyl)-3-fluoro-6,11-dihydrodibenz[b,e]oxepin:

(a) To a solution of 4.0 g of 1-cinnamylpiperazine in 20 ml of chloroform is added a solution of 2.0 g of 11-choloro-3-fluoro-6,11-dihydrodibenz[b,e]oxepin, which is prepared in Reference Example 1, in 10 ml of chloroform under ice cooling and then the mixture is stirred at room temperature for 2 hours. The reaction mixture is poured into 5% aqueous sodium hydrogen carbonate and the mixture is extracted with chloroform. After the extract is washed with water, chloroform is distilled off. The residue is subjected to silica-gel chromatography and eluted with chloroform to give .5 g of the objective compound as an oil. Mass spectrum m/z: 414(M+).

(b) To a solution of 1.4 g of the above free base in 10 ml of ethanol is added 0.6 g of oxalic acid to dissolve with heating and then the solution is cooled. Precipitated crystals are collected by filtration and recrystalized from ethanol to give the objective oxalate. Melting point 204°-207° C. (dec.).

(c) To a solution of 1.4 g of the above free base in 10 ml of ethanol is added 0.8 g of maleic acid to dissolve and then diethyl ether is added. Precipitated crystals are collected by filtration and recrystallized from ethanol-diethyl ether to give 3/2 maleate monohydrate of the objective compound (compound 1). Melting point 133°-135° C.

(d) (Z)-1-cinnamylpiperazine is employed in place of 1-cinnamylpiperazine (E form) in the above (a) and the reaction and the treatment are conducted in the same manner as in the procedure (a) to give (Z)-11-(4-cinnamyl-1-piperazinyl)-3-fluoro-6,11-dihydrodibenz[b,e]oxepin as an oil. Mass spectrum m/z: 414(M+). This free base is treated by the above procedure (c) and recrystallized from ethanoldiethyl ether to give corresponding 2 maleate. Melting point 121°-124° C.

EXAMPLE 2

Preparation of 11-(4-cinnamyl-1-piperazinyl)-2-methoxy-6,11-dihydrodibenz[b,e]oxepin:

(a) A mixture of 2 g of 2-methoxy-6,11-dihydrodibenz[b,e]oxepin-11-ol, which is prepared in Reference Example 2, and 10 g of thionylchloride is stirred at room temperature for 10 minutes and then added with dried toluene and the solvent is distilled off under reduced pressure. The residue is added with 30 ml of dichloromethane and cooled to 0° C. Thereto 1.8 g of 4-cinnamyl-1-piperazine is added and the mixture is stirred at room temperature for 3 hours. The reaction mixture is poured into a saturated aqueous solution of sodium hydrogen carbonate and extracted with chloroform. After the extract is dried over potassium carbonate and the solvent is distilled off under reduced pressure, the residue is subjected to silica-gel chromatography and eluted with chloroform. The fraction of the objective compound is collected and the solvent is distilled off under reduced pressure. The residue is recrystallized from diethyl ether-hexane to give 2.0 g of the objective compound. Melting point 85°–89° C.

(b) To a solution of 2.0 g of the above free base in 5 ml of ethanol is added 1.2 g of fumaric acid to dissolve and then diethyl ether is added. Precipitated crystals are collected by filtration and recrystallized from ethanol-diethyl ether to give 2 fumarate of the objective compound (compound 2). Melting point 158°–160° C.

(c) To a solution of 2.0 g of the above free base in 5 ml of ethanol is added 1.2 g of maleic acid to dissolve and then diethyl ether is added. Precipitated crystals are collected by filtration and recrystallized from ethanol-diethyl ether to give 2 maleate ½ hydrate. Melting point 142°–145° C.

(d) A solution of 2.0 g of the above free base in 5 ml of ethanol is poured into a solution of 1.5 g of oxalic acid in diethyl ether (300 ml) with stirring to give 2 oxalate 3/4 hydrate of the objective compound. Melting point 106°–112° C.

EXAMPLE 3

Preparation of 11-(4-cinnamyl-1-piperazinyl)-2-hydroxy-6,11-dihydrodibenz[b,e]oxepin:

A mixture of 3 g of 2-(dimethyl-t-butylsilyloxy)-6,11-dihydrodibenz[b,e]oxepin-11-ol, which is prepared in Reference Example 3, and 10 g of thionyl chloride is stirred at room temperature for 10 minutes and then added with dry toluene. The solvent is distilled off under reduced pressure and the residue is added with dichloromethane and cooled to 0° C. Thereto 2.0 g of 4-cinnamyl-1-piperazine is added and the mixture is stirred at room temperature for 3 hours. The reaction mixture is poured into a saturated aqueous sodium hydrogen carbonate and the mixture is extracted with chloroform. After the extract is dried over potassium carbonate and the solvent is distilled off under reduced pressure, the residue is subjected to silica-gel chromatography and eluted with chloroform to give 3.1 g of 11-(4-cinnamyl-1-piperazinyl)-2-(dimethyl-t-butylsilyloxy)-6,11-dihydrodibenz[b,e]oxepin (oil, Mass spectrum m/z: 526(M+), melting point of 2 maleate thereof : 138°–139° C.). To a solution of 2.0 g of this compound in 20 ml of tetrahydrofuran is added 1.5 g of tetra-n-butylammonium fluoride and the mixture is stirred for 30 minutes. To this solution is added 30 ml of water and the mixture is extracted with chloroform. After the extract is dried over magnesium sulfate, the solvent is distilled off under reduced pressure and the residue is subjected to silica-gel chromatography and eluted with chloroform : methanol (50:1) to give 1.1 g of the objective compound as an oil. Mass spectrum m/z: 412 (M+).

A solution of 1.0 g of the above free base in 3 ml of ethanol is added to a solution of 0.7 g of fumaric acid in diethyl ether with stirring. Precipitated crystals are collected by filtration to give fumarate of the objective compound (compound 3). Melting point 162°–166° C.

EXAMPLE 4

The procedure of Reference Example 2 is repeated, except that the disubstituted 6,11-dihydrodibenz[b,e]oxepin-11-ones prepared in Reference Examples 4 to 7 are used as the starting materials, there are produced disubstituted 6,11-dihydrodibenz[b,e]oxepin-11-ols, which are treated in the same manner as described in Example 2 to give the following compounds.

| Comp. No. | $R_1$ | $R_2$ | $R_3$ | $R_4$ | n | Q | mp (°C.) |
|---|---|---|---|---|---|---|---|
| 4 | H | F | H | F (8-posit.) | — | 2 maleate | 134–136 |
| 5 | H | H | F | F (7-posit.) | ½ | 2 oxalate | 182–184 |
| 6 | H | H | F | F (9-posit.) | — | 2 maleate | 144–146 |
| 7 | MeO | H | H | H | ¾ | 3 maleate | 149–150 |

MeO: methoxy
*Recrystallization solvent: ethanol-diethyl ether

EXAMPLE 5

Preparation of 2-fluoro-11-[4-? 3-(2-thienyl)-2-propenyl]-1-piperazinyl]-6,11-dihydrodibenz[b,e]oxepin:

(a) To a solution of 2.0 g of 3-(2-thienyl)-2-propen-1-ol in 20 ml of methylene chloride are added 7.0 g of triethylamine and 2.2 g of methanesulfonyl chloride at 0° C. and the mixture is stirred at the same temperature for 1 hour. Thereto a solution of 4.3 g of 2-fluoro-11-(1-piperazinyl)-6,11dihydrodibenz[b,e] oxepin, prepared in Reference Example 8, in 10 ml of methylene chloride is added at 0° C. and the mixture is stirred at the same temperature for 2 hours. The reaction mixture is added with 10% aqueous potassium carbonate and the mixture is extracted with chloroform. After the extract is successively washed with water and a saturated saline solution and dried over anhydrous potassium carbonate, the solvent is distilled off under reduced pressure. The residue is subjected to silica-gel chromatography and eluted with chloroform to give 3.1 g of the objective compound as an oil. Mass spectrum m/z: 420(M+).

(b) A solution of 2.0 g of the above free base in 2 ml of ethanol is added dropwise to a solution of 1.4 g of oxalic acid in 500 ml of diethyl ether. Precipitate is collected by filtration to give 2 oxalate.½ hydrate of the objective compound (compound 8). Melting point 97°–105° C.

EXAMPLE 6

The following compounds are obtained in the same manner as in Example 5.

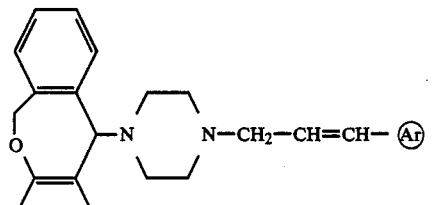

| Comp. No. | Ar | n | .nH₂O .Q Q | mp (°C.) |
|---|---|---|---|---|
| 9 | pyridyl | 5/2 | 2 oxalate | 93–110 |
| 10 | pyridyl | — | 3 maleate | 109–111 |
| 11 | thienyl | ½ | 3/2 oxalate | 97–105 |

*Recrystallization solvent: ethanol-diethyl ether

REFERENCE EXAMPLE 9

Preparation of 11-?
4-(3,-methoxycinnamyl)-1-piperazinyl-3-fluoro-6-11dihydrodibenz[b,e]oxepin (compound A):

Starting from 11-chloro-3-fluoro-6,11-dihydrodibenz[b,e]oxepin, prepared in Reference Example 1, and (1-(3'-methoxycinnamyl)-piperazine, there is produced 2 maleate of the objective compound in the same manner as in Example 1. Melting point 136°–140? C. (recrystallized from ethanol-diethylether).

REFERENCE EXAMPLE 10

Preparation of
11-(4-cinnamyl-1-piperazinyl)-3-methyl-6,11-dihydrodibenz[b,e]oxepin (compound B):

Starting from 11-chloro-3-methyl-6,11-dihydrodibenz[b,e]oxepin, which is prepared from 3-methylphenol and phthalide in the same manner as in Reference Example 1, and 1-cinnamylpiperazine, there is produced 2-oxalate.½ hydrate of the objective compound in the same manner as in Example 1. Melting point 195-200° C. (recrystallized from ethanol-diethyl ether).

EXAMPLE 7

Preparation of tablets:

| | |
|---|---|
| 11-(4-Cinnamyl-1-piperazinyl)-3-fluoro-6,11-dihydrodibenz[b,e]oxepin · 3/2 maleate · 1 hydrate (compound 1) | 5 g |
| Corn starch | 33 g |
| Lactose | 75 g |
| Crystalline cellulose | 30 g |
| Hydroxypropyl cellulose | 5 g |
| Light silicic anhydride | 1 g |
| Magnesium stearate | 1 g |

In accordance with the conventional procedure, the above ingredients are mixed and granulated and compressed to prepare 1000 tablet cores (150 mg in each). These are coated in accordance with the conventional procedure, employing hydroxypropyl methyl cellulose, talc, titanium oxide and sorbitan monooleate to prepare film-coated tablets.

EXAMPLE 8

Preparation of capsules:

| | |
|---|---|
| 11-(4-Cinnamyl-1-piperazinyl)-3-fluoro-6,11-dihydrodibenz[b,e]oxepin · 3/2 maleate · 1 hydrate (compound 1) | 10 g |
| Corn starch | 44 g |
| Lactose | 20 g |
| Crystalline cellulose | 25 g |
| Talc | 0.5 g |
| Magnesium stearate | 0.5 g |

In accordance with the conventional procedure, the above ingredients are mixed and granulated and filled in 1000 capsules to prepare capsules (100 mg in each).

INDUSTRIAL APPLICABILITY

As mentioned above, the compound of the formula (I) of the present invention or the physiologically acceptable acid addition salts thereof have an excellent protective effect against cerebral anoxia and some of them have also an inhibitory effect on lipid peroxidation of mitochondrial membrane of brain and an anti-convulsant activity and are useful as an agent for the treatment of cerebral diseases caused by hypoxia in mammals including human.

We claim:

1. A compound represented by the general formula (I):

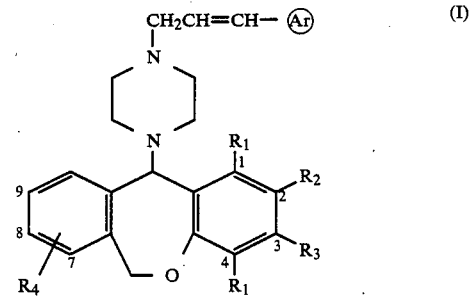

wherein $R_1$ is hydrogen atom or methoxy group, $R_2$ is hydrogen atom, methoxy group, hydroxy group or fluorine atom, $R_3$ is hydrogen atom or fluorine atom, $R_4$ is hydrogen atom or fluorine atom at 7-, 8- or 9-position, and Ar is a benzene ring, a thiophene ring or a pyridine ring, provided that (i) at least two of $R_1$, $R_2$, $R_3$ and $R_4$ are hydrogen atoms, (ii) $R_2$ or $R_3$ is fluorine atom when $R_4$ is fluorine atom, (iii) $R_1$, $R_3$ and $R_4$ are hydrogen atoms when $R_2$ is methoxy group or hydroxy group, (iv) $R_2$ and $R_3$ are not simultaneously fluorine atoms, and (v) $R_2$ is hydrogen atom or fluorine atom, $R_3$ is hydrogen atom or fluorine atom, and both $R_1$ and $R_4$ are hydrogen atoms when Ar is a thiophene ring or a pyridine ring, or a physiologically acceptable acid addition salt thereof.

2. A compound represented by the general formula (I-a):

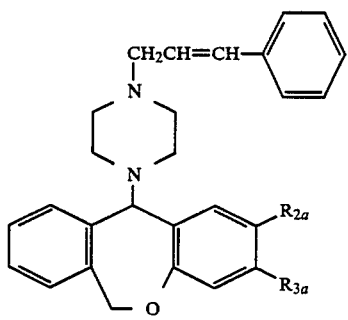

(I-a)

wherein $R_{2a}$ is hydrogen atom or methoxy group, and $R_{3a}$ is hydrogen or fluorine atom, provided that one of $R_{2a}$ and $R_{3a}$ is always hydrogen atom, or a physiologically acceptable acid addition salt thereof.

3. The compound according to claim 2, which is 11-(4-cinnamyl-1-piperazinyl)-3-fluoro-6,11-dihydrodibenz[b,e]oxepin, or a physiologically acceptable acid addition salt thereof.

4. The compound according to claim 2, which is 11-(4-cinnamyl-1-piperazinyl)-2-methoxy-6,11-dihydrodibenz[b,e]oxepin, or a physiologically acceptable acid addition salt thereof.

5. A compound represented by the general formula (I-b):

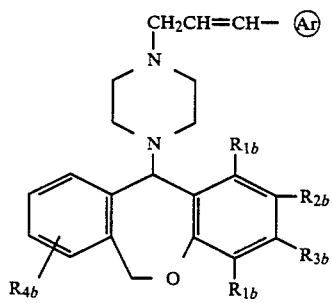

(I-b)

wherein $R_{1b}$ is hydrogen atom or methoxy group, $R_{2b}$ is hydrogen atom, hydroxy group or fluorine atom, $R_{3b}$ is hydrogen atom or fluorine atom, $R_{4b}$ is hydrogen atom or fluorine atom at 7-, 8- or 9-position, and (Ar) is a benzene ring, a thiophene ring or a pyridine ring, provided that (i) at least two of $R_{1b}$, $R_{2b}$, $R_{3b}$ and $R_{4b}$ are hydrogen atoms, (ii) $R_{2b}$ or $R_{3b}$ is fluorine atom when $R_{4b}$ is fluorine atom, (iii) $R_{1b}$, $R_{3b}$ and $R_{4b}$ are hydrogen atoms when $R_{2b}$ is hydroxy group, (iv) $R_{2b}$ and $R_{3b}$ are not simultaneously fluorine atoms, (v) $R_{2b}$ is hydrogen atom or fluorine atom, $R_{3b}$ is hydrogen atom or fluorine atom, and $R_{1b}$ and $R_{4b}$ are both hydrogen atoms when (Ar) is a thiophene ring or a pyridine ring, and further excluding the compound in which (Ar) is a benzene ring, $R_{3b}$ is fluorine atom, and $R_{1b}$, $R_{2b}$ and $R_{4b}$ are hydrogen atoms, or a physiologically acceptable acid addition salt thereof.

6. The compound according to claim 5, which is 11-(4-cinnamyl-1-piperazinyl)-2-hydroxy-6,11-dihydrodibenz[b,e]oxepin, or a physiologically acceptable acid addition salt thereof.

7. A pharmaceutical composition for treatment of cerebral diseases caused by hypoxia comprising as an active ingredient an anti-cerebral hypoxia effective amount of a compound or a physiologically acceptable acid addition salt thereof as set forth in any one of claims 1 to 6 and a pharmaceutical carrier therefor.

8. The agent according to claim 7, which is in the form of tablets or capsules.

9. A method for the treatment of cerebral diseases caused by hypoxia in mammals, which comprises administering an anti-cerebral hypoxia effective amount of a compound or a physiologically acceptable acid addition salt thereof as set forth in any one of claims 1 to 6 to the mammals to be treated.

10. A pharmaceutical composition for the treatment of cerebral diseases caused by hypoxia comprising as an active ingredient an anti-cerebral hypoxia effective amount of 11-(4-cinnamyl-1-piperazinyl)-3-fluor-6,11-dihydrodibenz[b,e]-oxepin, or a physiologically acceptable acid addition salt thereof in association with a pharmaceutical carrier.

11. A method for treatment of cerebral diseases caused by hypoxia in mammals, which comprises administering to said mammals an anti-cerebral hypoxia effective amount of 11-(4-cinnamyl-1-piperazinyl)-3-fluoro-6,11-dihydrodibenz[b,e]-oxepin, or a physiologically acceptable acid addition salt thereof.

* * * * *

UNITED STATES PATENT AND TRADEMARK OFFICE
CERTIFICATE OF CORRECTION

PATENT NO. : 4,889,858
DATED : December 26, 1989
INVENTOR(S) : Hitoshi Uno, et al.

It is certified that error appears in the above-identified patent and that said Letters Patent is hereby corrected as shown below:

Column 8, line 57: "o" should read as --of--

Column 18, line 24: ".5g" should read as --1.5g--

Column 20, line 33: "[4-?3-" should read as --[4-[3- --

Column 20, line 43: "[b,e?" should read as --[b,e]--

Column 21, line 15: "mp (°C.)" should read as --mp (°C.)*--

Column 21, line 33: "11-? 4-(3," should read as --11-[4-(3'--

Column 21, line 41: "140? C." should read as --140°C--

Signed and Sealed this

Nineteenth Day of February, 1991

*Attest:*

HARRY F. MANBECK, JR.

*Attesting Officer*  *Commissioner of Patents and Trademarks*